United States Patent [19]

Yokomichi et al.

[11] 4,349,681
[45] Sep. 14, 1982

[54] 2-AMINO-3-CHLORO-5-TRIFLUOROME-THYLPYRIDINE

[75] Inventors: Isao Yokomichi, Moriyama; Takahiro Haga, Kusatsu; Kuniaki Nagatani, Kusatsu; Toshio Nakajima, Kusatsu, all of Shiga, Japan

[73] Assignee: Ishihara Sangyo Kaisha, Ltd., Osaka, Japan

[21] Appl. No.: 218,971

[22] Filed: Dec. 22, 1980

[30] Foreign Application Priority Data

Dec. 24, 1979 [JP] Japan ................................. 54-167986

[51] Int. Cl.$^3$ .................. C07D 213/72; C07D 211/72
[52] U.S. Cl. ..................................... 546/304; 546/311
[58] Field of Search ................................ 546/304, 311

[56] References Cited

U.S. PATENT DOCUMENTS 3,787,420  1/1974  Torba ................................. 546/304

Primary Examiner—Henry R. Jiles
Assistant Examiner—Robert C. Whittenbaugh
Attorney, Agent, or Firm—Sughrue, Mion, Zinn, Macpeak and Seas

[57] ABSTRACT

A novel compound, 2-amino-trifluoromethyl-halogenopyridine, is provided, which is prepared by amination of a 2-halogeno-trifluoromethyl-halogenopyridine or by halogenation of 2-amino-trifluoromethylpyridine. This compound is useful as an intermediate for synthesis of agricultural chemicals and medicines.

1 Claim, No Drawings

2-AMINO-3-CHLORO-5-TRIFLUOROMETHYL-PYRIDINE

BACKGROUND OF THE INVENTION

This invention relates to a novel compound, 2-amino-trifluoromethyl-halogenopyridine and a process for producing the same by reacting a 2-halogeno-trifluoromethyl-halogenopyridine and ammonia or by reacting a 2-amino-trifluoromethylpyridine and a halogenating agent.

The 2-amino-trifluoromethyl-halogenopyridine of this invention is useful as an intermediate for synthesis of agricultural chemicals and medicines.

A number of pyridine derivatives have hitherto been known to be useful intermediates for the production of organic compounds. For example, 2-amino-5-trifluoromethylpyridine as a starting material for the production of imidazopyridines and a process for the production thereof from 5-carboxy-2-hydroxypyridine are described in U.S. Pat. No. 3,681,369.

The pyridine compound of this invention is different in chemical structure from such known pyridine derivatives and has a novel utility.

SUMMARY OF THE INVENTION

A primary object of this invention is to provide a 2-amino-trifluoromethyl-halogenopyridine compound represented by the following formula (I):

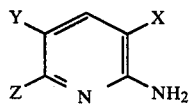

wherein either X or Y is a trifluoromethyl group, and at least one of X, Y and Z is a halogen atom, with the remainder being a halogen atom or a hydrogen atom.

Another object of this invention is to provide a process for the production of the 2-amino-trifluoromethyl-halogenopyridine compound of the formula (I), which comprises reacting a 2-halogeno-trifluoromethyl-halogenopyridine represented by the following formula (II):

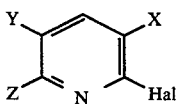

wherein X, Y and Z are the same as defined above, and Hal is a halogen atom, and ammonia.

A further object of this invention is to provide a process for the production of a 2-amino-trifluoromethyl-halogenopyridine compound represented by the following formula (IV):

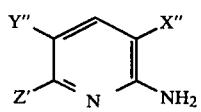

wherein either X″ or Y″ is a trifluoromethyl group, with the remainder being a halogen atom, and Z′ is a hydrogen atom or a halogen atom, which comprises reacting a 2-halogeno-trifluoromethylpyridine compound represented by the following formula (III):

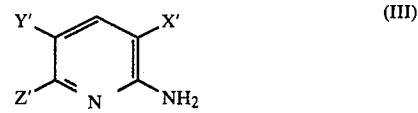

wherein either X′ or Y′ is a trifluoromethyl group, with the remainder being a hydrogen atom, and Z′ is the same as defined above, and a halogenating agent.

DETAILED DESCRIPTION OF THE INVENTION

In the above formulae (I), (II), (III) and (IV), examples of the halogen atom include fluorine, chlorine, bromine and iodine.

Examples of 2-amino-trifluoromethyl-halogenopyridines of this invention include 2-amino-3-chloro-5-trifluoromethylpyridine (m.p. 90°–92° C.), 2-amino-3-bromo-5-trifluoromethylpyridine (m.p. 99°–100° C.), 2-amino-5-trifluoromethyl-6-chloropyridine (m.p. 111°–113° C.), 2-amino-3-trifluoromethyl-6-chloropyridine (m.p. 99°–101° C.), 2-amino-5-trifluoromethyl-6-fluoropyridine, 2-amino-3-trifluoromethyl-5-bromopyridine (m.p. 84°–86° C.), 2-amino-3-trifluoromethyl-5-chloropyridine (m.p. 85°–87° C.), 2-amino-3-trifluoromethyl-5-bromo-6-chloropyridine (m.p. 110°–112° C.), 2-amino-3-bromo-5-trifluoromethyl-6-chloropyridine (m.p. 114°–116° C.), 2-amino-3,6-dichloro-5-trifluoromethylpyridine (m.p. 110°–111° C.), and so forth.

The 2-amino-trifluoromethyl-halogenopyridine of this invention can be usually produced by the following Method (1) or (2).

Method (1): Amination of 2-Halogeno Compound

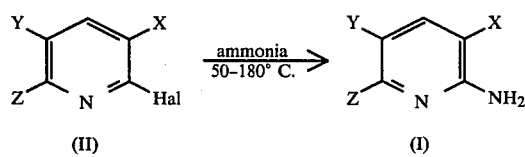

In the formulae (I) and (II), X, Y, Z and Hal are the same as defined hereinbefore.

A 2-halogeno-trifluoromethyl-halogenopyridine compound of the formula (II) and aqueous ammonia which has previously been prepared by dissolving ammonia in water are placed in a closed vessel, e.g., an autoclave, or liquid ammonia is introduced into the 2-halogeno-trifluoromethyl-halogenopyridine compound, followed by the reaction at a temperature of 50° to 180° C., preferably 100° to 150° C. When the reaction temperature exceeds the above specified upper limit, the desired product tends to decompose, whereas when it is below the lower limit, the reaction does not proceed sufficiently.

Where aqueous ammonia is used as the ammonia, one having a concentration of 20% or more, preferably 28 to 40% is usually used. The pressure during the reaction reaches about 2 to 30 atms. due to a temperature's increase inside the closed vessel.

The amount of ammonia used is 1 mol or more, preferably 3 to 10 mols, per mol of the 2-halogeno-trifluoromethyl-halogenopyridine. The time of reaction is 3 hours or longer, preferably 3 to 12 hours.

The substitution reaction of the halogen atom by the amino group occurs at the 2-position of the pyridine nucleus, but when the halogen atom is present at the 6-position, it also occurs at the 6-position.

The reaction product thus obtained is allowed to cool and usually extracted with a solvent, such as methylene chloride, benzene, diethyl ether, or the like. The solvent is then evaporated off, and if necessary, usual distillation is carried out to obtain the desired product, 2-amino-trifluoromethyl-halogenopyridine. The desired product in the reaction product is obtained as an oily substance or crystals, and thus, impurities can be removed by the above extraction.

Further, in the event that aqueous ammonia is used as the ammonia, the desired product may be contained in the aqueous phase of the reaction product, but the desired product can sufficiently be recovered by the above extraction.

Method (2): Halogenation of 2-Amino Compound

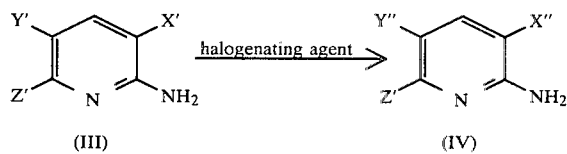

In the formulae (III) and (IV), X', X", Y', Y" and Z' are the same as defined hereinbefore.

2-Amino-trifluoromethylpyridine or a 2-amino-6-halogeno-trifluoromethylpyridine which can be prepared by the Method (1) above or equivalent method thereto is reacted with a halogenating agent to form a desired 2-amino-trifluoromethyl-monohalogeno-pyridine or 2-amino-trifluoromethyl-dihalogenopyridine. This reaction is usually carried out by introducing the halogenating agent (usually, chlorine gas or bromine) into a solution prepared by dissolving the above starting pyridine in acetic acid, hydrochloric acid, sulfuric acid or hydrobromic acid, and if necessary, by further adding thereto other inert solvent.

For example, in the case of chlorination, the starting pyridine is dissolved in a suitable concentration of hydrochloric acid in an amount of 4 to 10 mols per mol of the starting pyridine, and chlorine gas is introduced into the solution thus prepared while maintaining the temperature of the system at 0° to 100° C., preferably 0° to 50° C. The amount of the chlorine used is usually 1.1 to 5 mols, preferably 1.5 to 3 mols, per mol of the starting pyridine.

In the case of bromination, the starting pyridine is dissolved in an aqueous solution of acetic acid or hydrobromic acid in an amount of 5 to 20 mols per mol of the starting pyridine, and bromine is dropwise added thereto while maintaining the temperature of the system at 10° to 60° C., preferably 35° to 45° C. The amount of the bromine used is usually 1 to 2 mols, preferably 1 to 1.2 mols, per mol of the starting pyridine.

The reaction is usually completed in 0.5 to 10 hours although it may vary depending upon the reaction conditions.

The substitution reaction of the hydrogen atom by the halogen atom occurs at the β-position of the pyridine nucleus at which no trifluoromethyl group exists.

The present invention will be described in detail by reference to the following Examples which, however, do not limit the present invention in any way.

EXAMPLE 1

Preparation of 2-Amino-3-chloro-5-trifluoromethylpyridine 6.5 g of 2,3-dichloro-5-trifluoromethylpyridine and 20 ml of 28% aqueous ammonia were placed in a 50 ml autoclave, and the mixture was reacted for 24 hours at 100° C., and further for 5 hours at 125° C. (inner pressure: about 2 atms.). After completion of the reaction, the reaction product was allowed to cool to obtain crystals. The thus obtained crystals were then washed with water and dried to obtain 1.5 g of 2-amino-3-chloro-5-trifluoromethylpyridine having a melting point of 90° to 92° C.

EXAMPLE 2

Preparation of 2-Amino-3-trifluoromethyl-6-chloropyridine and 2-Amino-5-trifluoromethyl-6-chloropyridine 6.48 g of 2,6-dichloro-3-trifluoromethylpyridine and 18 ml of 28% aqueous ammonia were placed in a 50 ml autoclave, and the mixture was reacted for 24 hours at 90° C. (inner pressure: about 2 atms.). After completion of the reaction, the reaction product was allowed to cool, and methylene chloride was added thereto to thereby extract the desired product and the unreacted starting material. The methylene chloride in the extract was evaporated off, and the separation was carried out by silica gel column chromatography using firstly n-hexane and then methylene chloride as eluents. Thus, 1.12 g of 2-amino-3-trifluoromethyl-6-chloropyridine having a melting point of 99° to 101° C. and 1.37 g of 2-amino-5-trifluoromethyl-6-chloropyridine having a melting point of 111° to 113° C. were obtained.

EXAMPLE 3

Preparation of 2-Amino-3,6-dichloro-5-trifluoromethylpyridine

In a 200 ml four necked flask equipped with a thermometer, a stirrer and a reflux condenser were placed 7 g of 2-amino-5-trifluoromethyl-6-chloropyridine, 10 ml of carbon tetrachloride and 70 ml of 20% sulfuric acid to give a homogeneous solution. Chlorine gas was introduced thereinto while cooling the flask at 0° C., and the reaction was carried out for 4 hours. After confirming the completion of the reaction by thin layer chromatography, the reaction product was poured into ice water and neutralized with a potassium hydroxide solution. 50 ml of methylene chloride was added thereto, followed by washing with water. The organic phase was dried over anhydrous sodium sulfate, and the solvent was evaporated off. The solid thus obtained was washed with n-hexane to obtain 6.7 g of the desired product.

EXAMPLE 4

Preparation of 2-Amino-3-bromo-5-trifluoromethylpyridine

In a 100 ml four necked flask equipped with the same equipments as those used in Example 3 were placed 3 g of 2-amino-5-trifluoromethylpyridine and 30 ml of acetic acid to provide a homogeneous solution. 4.4 g of bromine was dropwise added thereto while cooling the flask with ice water at 10° to 20° C., and after completion of the dropwise addition, the mixture was reacted for 1 hour. The reaction product was poured into 200 ml of water, washed with an aqueous solution of sodium thiosulfate and extracted with methylene chloride. The methylene chloride layer was dried over anhydrous sodium sulfate, and the solvent was evaporated off. The solid thus obtained was washed with n-hexane to obtain 3.5 g of the desired product.

The 2-amino-trifluoromethyl-halogenopyridine per se of this invention has no physiological activity, but can be chemically converted into a substance having high physiological activity. It has been confirmed that the 2-amino-trifluoromethyl-halogenopyridine is a useful intermediate for synthesis of agricultural chemicals and medicines.

For example, 2-amino-3-chloro-5-trifluoromethylpyridine is reacted with 2,6-difluorobenzoylisocyanate in toluene at 40° C. for 30 minutes, whereby N-(2,6-difluorobenzoyl)-N'-(3-chloro-5-trifluoromethyl-2-pyridyl)urea having a melting point of 214° to 217° C. can be obtained. This compound is effective in inhibiting and controlling various pests, particularly noxious insects. For example, in the insecticidal testing of the compound in a concentration of 800 ppm against larvae of diamondback moth in 3rd or 4th instar, a 100% insecticidal effect can be obtained.

Also, 2-amino-6-chloro-3-trifluoromethylpyridine is dissolved in dimethylformamide, and potassium hydroxide is added thereto. A dimethylformamide solution of 2-chloro-3,5-dinitrobenzotrifluoride is further added thereto to cause the reaction for 3 hours whereby N-(2-chloro-5-trifluoromethyl-6-pyridyl)-2,4-dinitro-6-trifluoromethylaniline having a melting point of 129° to 131° C. can be obtained. This compound is effective in inhibiting and controlling various microorganisms, particularly noxious pathogenic microorganisms in agriculture and horticulture. For example, in the insecticidal testing of the compound in a concentration of 100 ppm against *Sphaerotheca fuliginea* and *Rhizoctonia solani* of rice plant, a control value of 100% is exhibited.

While the invention has been described in detail and with reference to specific embodiments thereof, it will be apparent to one skilled in the art that various changes and modifications can be made therein without departing from the spirit and scope thereof.

What is claimed is:
1. 2-Amino-3-chloro-5-trifluoromethylpyridine.

* * * * *